US006838786B1

(12) United States Patent
Frescaline et al.

(10) Patent No.: US 6,838,786 B1
(45) Date of Patent: Jan. 4, 2005

(54) DEVICE AND METHOD FOR GENERATING INTENSE AND BRIEF CONTROLLED VARIATIONS OF MAGNETIC PRESSURE IN A SAMPLE OF SOLID MATERIAL

(75) Inventors: Laurent Frescaline, Saint-Cere (FR); Gilles Avrillaud, St-Jean-Lagineste (FR)

(73) Assignee: I T H P P, Gramat (FR)

( * ) Notice: Subject to any disclaimer, the term of this patent is extended or adjusted under 35 U.S.C. 154(b) by 397 days.

(21) Appl. No.: 10/019,943

(22) PCT Filed: Jun. 28, 2000

(86) PCT No.: PCT/FR00/01805

§ 371 (c)(1),
(2), (4) Date: Jan. 7, 2002

(87) PCT Pub. No.: WO01/05033

PCT Pub. Date: Jan. 18, 2001

(30) Foreign Application Priority Data

Jul. 7, 1999 (FR) .............................................. 9908771

(51) Int. Cl.[7] ................................................ H03K 3/00
(52) U.S. Cl. ........................... 307/106; 72/56; 307/108; 333/20
(58) Field of Search ............................... 307/106, 108; 72/56; 333/20

(56) References Cited

U.S. PATENT DOCUMENTS 5,621,255 A * 4/1997 Leon et al. ................. 307/106

5,860,306 A * 1/1999 Daehn et al. ................. 72/56

OTHER PUBLICATIONS

R. Dormeval et al., "Comportement Dynamique Sous Choc De La Matiere", Revue scientifique et technique de la Direction des applications militaires, No. 5, Sep. 1992, pp. 77–90.

B. Etlicher et al., "Low Inductance Triggered Multichannel Surface Switch for Inductive Energy Storage Generator", 10th IEEE Pulsed power conference Albuquerque New Mexico, 1995, pp 243–248.

Kim A.A. et al., "Multi Gap, Multi Channel Spark Switches", 11 IEEE Pulsed power conference Baltimore, Maryland, 1997, pp 862–867.

* cited by examiner

*Primary Examiner*—Robert L. DeBeradinis
(74) *Attorney, Agent, or Firm*—Young & Thompson

(57) ABSTRACT

A device and a method for generating intense and brief variations of magnetic pressure, predetermined and controlled, capable of being isentropic inside a sample (23) of solid material. An electromagnetic cell (1) includes a flat parallel line of conductive material having two branches (4, 5) in the form of planar plates, of similar shapes and dimensions, separated from each other by a distance of not more than 3 mm, one of which (4) bears the sample (23) rigidly fixed on the branch (4), the two branches (4, 5) being electrically connected to each other by an end junction strip (7), and electrically connected, opposite the end junction strip, to elements (2, 3) generating electric current pulses so as to produce in less than 500 ns an electric current flowing in the electronic cell (1).

30 Claims, 5 Drawing Sheets

DEVICE AND METHOD FOR GENERATING INTENSE AND BRIEF CONTROLLED VARIATIONS OF MAGNETIC PRESSURE IN A SAMPLE OF SOLID MATERIAL

This application is a national stage application of PCT/FR00/01805 filed Jun. 28, 2000 and claims priority from French Application 99/08771 filed Jul. 7, 1999.

BACKGROUND OF THE INVENTION

The invention concerns a device and method to generate intense and brief variations, but nevertheless predetermined and controlled, of magnetic pressure, especially of at least one gigapascal and able to range up to five terapascals, in a period able to be between 1 ns and 500 ns, inside a sample of a solid material.

The application of these intense brief pressure variations inside a solid material make it possible to study their behaviour and analyse the various complex phenomena which may occur when the solid material is subjected to extreme stresses (phase changes, determination of state equations and laws of behaviour, degradations, instabilities, breakages . . . ).

Known devices able to generate intense and brief variations inside solid materials (cf. "COMPORTEMENT DYNAMIQUE SOUS CHOC DE LA MATIERE" by R. Dormeval and others, Scientific and Technical Review for the Management of military applications, issue 5, September 1992, pp 77–90) consist of impact generators (launchers, explosives, electromagnetic guns . . . ) or diamond anvil presses. In the first case, it is extremely difficult to accurately control the parameters of the pressure profile and it is impossible to generate isentropic pressure variations. In particular, there exists an electric gun including a parallel flat line fed by an electric current pulse generator so as to make a cutting aluminium sheet explode and projecting an isolation disk at high speed. The explosion of the sheet basically occurs under the effect of the heat energy resulting from the rise of the intensity of the current which lasts more than 600 ns and circulates inside the entire thickness of the sheet which is less than skin thickness. As for diamond anvil presses, these are extremely complex expensive devices which also have the drawback of only allowing a small amount of space around the sample, thus limiting the possibilities for analysing mechanical behaviour.

SUMMARY OF THE INVENTION

Accordingly, the invention seeks to mitigate these drawbacks by offering a device and method able to generate intense and brief magnetic pressure variations according to a predetermined and controlled intensity and period, said period being less than 500 ns inside a sample of a solid material and moreover with magnetic pressure variations which may be isentropic effected at reduced cost as well as in a controlled impact state (impact wave) whilst leaving free the space around the sample so as to enable the latter to be analysed.

In particular, the invention seeks to provide a device occupying less space and having a low energy consumption with regard to its performances.

Also, the invention seeks to provide in particular a device and method generating an approximately uniform pressure field inside the sample.

Also, the invention seeks to provide a device and method making it possible to attain inside a sample of a solid material predetermined pressure variations of between 1 Gpa and 5 Tpa—especially between 100 Gpa and 1 Tpa—in a period of between 1 ns and 500 ns and in particular between 10 ns and 300 ns.

The invention also seeks to provide in particular a device such as the one mentioned above of the electromagnetic type and with a total spatial requirement of less than 110 m$^3$, especially about 1 m$_3$, and developing energy in the electromagnetic cell of less than 500 kJ and in particular about 10 kJ.

In order to attain this aim, the invention concerns a device able to generate intense and brief magnetic pressure variations, predetermined and controlled, able to be isentropic inside a sample of a solid material, said device being characterised in that it includes means for generating electric current pulses of the high-power pulsed type, and an electromagnetic cell connected to the electric current pulse generation means, said electromagnetic cell bearing the sample and being adapted so that the sample is subjected to electromagnetic energy pulses resulting from applying to the electromagnetic cell electric current pulses originating from the electric current pulse generating means, in that the electromagnetic cell includes a flat parallel line of a conductive material including two branches in the form of planar plates having the same shapes and dimensions and separated from each other by a distance smaller than or equal to 3 mm and in particular smaller than 1 mm, one of which bearing the sample rigidly secured to said branch, at least approximately at the central portion, these two branches being electrically connected to each other by an end junction strip and electrically connected opposite the end junction strip to the electric current pulse generating means so as to allow an electric current to be established circulating from the electric current pulse generating means in one branch, then in the end strip and then in the other branch so as to come back to the electric current pulse generating means, and in that the electric current pulse generating means and the electromagnetic cell are adapted so that the build-up time $\tau$ in which the square of the intensity of the electric current circulating in the electromagnetic cell moves from 10% to 90% of its maximum value $I_{max}^2$ is included between 1ns and 500 ns. Advantageously and according to the invention, the build-up time $\tau$ is between 10 ns and 300 ns.

Advantageously and according to the invention, the electromagnetic cell is adapted so as to have an inductance of less than 4 nH and in particular less than 2 nH.

In addition, advantageously and according to the invention, the two branches are separated from each other, not by a vacuum, but by a dielectric material, especially a solid dielectric material or a solid/liquid dielectric material.

The dielectric material needs to be selected so as to possess a dielectric pulse rigidity (maximum pulse electric field it is able to support per unit of thickness without disruptive breakdown) adapted to the sought-after performances.

Advantageously and according to the invention, the dielectric material has a pulse dielectric rigidity of more than 100 kV/mm. In addition, advantageously and according to the invention, the dielectric material extends laterally beyond the branches so as to prevent border disruptive breakdowns.

Advantageously and according to the invention, the dielectric material can be selected from a polyimide, a polyester or a high density polyethylene.

In the invention, the sample in which the pressure variations need to be generated is directly secured rigidly to one branch of the parallel flat line forming the electromagnetic cell. In this way, it is possible to generate pressure variations able to be isentropic which are intense and brief with predetermined characteristics (pressure value and duration) and able to be controlled simply and accurately. It is to be noted that these pressure variations mainly result, not from an electromechanical or heat effect (Joule effect), but basically from magnetic forces resulting from the established electric current and circulating in the line with a sufficiently short build-up time (about or less than 500 ns) so that the energy of the magnetic forces is preponderant with respect to the heat energy whose appearance is slower. Thus and unexpectedly, the invention makes it possible to generate extremely intense and brief pressure profiles, but nevertheless uniform and controlled in the sample and on the basis of a relatively weak electric power able to be provided by an inexpensive source occupying a small space.

It is to be noted in particular that the choice of a parallel loop flat line (and not from a coaxial electromagnetic structure) combined with isolation by a dielectric material (and not isolation under vacuum by a magnetic isolation) makes it possible to in fact reduce the space between the branches to an extremely small value corresponding to a line impedance, also small.

Advantageously and according to the invention, when the branches are separated by a dielectric material, the distance between the two branches is less than 1 mm and in particular about 500 μm. The electromagnetic cell can then be adapted to have an inductance of less than 2 nH. Thus, although isolation under vacuum is a priori regarded as better and necessary for the intense magnetic pressure values, and thus magnetic field and current intensity values since it does not require any dielectric rigidity limit, the invention has shown that on the other hand it is preferable to opt for a flat line with isolation by a dielectric material making it possible to reduce the value of the inductance which proves in practice to be preponderant despite the fact that the dielectric rigidity of the dielectric material limits the performances of the device.

In particular, the created magnetic pressure field is extremely homogeneous (when it varies according to the square of the radial distance in a coaxial electromagnetic structure).

In addition, advantageously and according to the invention, the electric current pulse generating means comprise:
- at least one pulsed high power electric current pulse generator including two outgoing electrodes called the first and second outgoing electrodes,
- an electric linking line including a first conductive plate extending between the first outgoing electrode of each generator and one of the branches of the electromagnetic cell, and a second conductive plate extending between the second outgoing electrode and the other branch of the electromagnetic cell. Advantageously and according to the invention, the plates of the linking line have basically the same shapes and dimensions, are parallel to each other and superimposed opposite each other and separated and isolated from each other. Advantageously and according to the invention, the plates of the linking line extend into the extension of the branches of the electromagnetic cell. Advantageously and according to the invention, the linking line is adapted so as to have an inductance of less than 5 nH. This linking line is thus able to minimise the outgoing inductance of the generator(s) and obtain increased performances.

Advantageously and according to the invention, the cross section of the junction strip perpendicular to the direction of the electric current is smaller than the cumulated cross section of the first or second electrodes so that the electric current density reaches its maximum value in the junction strip. In particular, the width (larger dimension perpendicular to the circulation direction of the electric current) of the junction strip is smaller than the cumulated width of the first or second electrodes.

Advantageously, the device is characterised in that the two branches are rectangular, the junction strip linking two rectilinear edges of the two, branches, and in that the plates of the electric linking line have a convergent shape in terms of width and/or thickness so that the current density has a maximum value in the branches of the electromagnetic cell.

Moreover, advantageously and according to the invention, the electric current pulse generating means include at least one multichannel spark switch able to distribute the electric energy along the cross section, especially along the width, of the branches of the electromagnetic cell. In this way, the outgoing inductance of the generator(s) is further minimised. Advantageously and according to the invention, a multichannel spark switch is inserted between each generator and the electromagnetic cell.

Advantageously and according to the invention, for each generator, an individual multichannel spark switch is inserted between the first outgoing electrode of this generator and the first plate of the linking line. Thus, there is the same number of spark switches as generators.

Advantageously and according to the invention, the device includes several spark switches in parallel, especially several generators in parallel and several spark switches in parallel, one for each generator.

In one advantageous variant of the invention, the device is characterised in that it includes at least one set of several generators and in that a common multichannel spark switch is inserted between all the first electrodes of the generators of the same group and the first plate of the linking line. Thus, switching control is simplified.

Furthermore, in the case in particular where the electric voltage values are extremely high (in particular more than 50 kV), the device includes, advantageously and according to the invention, at least one series multichannel spark switch, that is a spark switch including several successive series gaps.

Advantageously and according to the invention, the sample is placed and rigidly fixed in a housing of the branch bearing it.

In a first variant of the invention, the housing opens on the side of the space separating the two branches from each other so that a sample made of a conductive material can be placed in the housing so as to be in electric link with the branch bearing it, this sample having a face in contact with the space separating the two branches from each other, especially in contact with the dielectric material.

In a second variant of the invention, the housing has a bottom forming a conductive wall able to separate a sample made of a non-conductive or poor conductive material placed in the housing from the space separating the two branches from each other especially of the dielectric material. Advantageously and according to the invention, the thickness of the conductive wall is smaller than that of the branch bearing it. The conductive wall is made of a solid rigid material serving as a thrustor transmitting the magnetic thrust resulting from the electric current circulating in the line to the sample having one face in contact with the conductive wall.

Advantageously and according to the invention, the device includes means for adjusting the value of the inductance of the electromagnetic cell and/or that of the electric current pulse generating means. In particular, advantageously and according to the invention, the device includes means for adjusting the distance between the two branches. Thus, it is possible to insert a variable inductance on the linking line or on either of the two branches. The adjustment of inductance makes it possible to firstly vary the maximum value of the intensity of the current created in the electromagnetic cell under the effect of a current pulse, and secondly the build-up time $\tau'$ of this intensity. In effect, it is possible to write:

$$U \approx LI_{max}/\tau' \text{ and } \tau' \approx \pi/2\sqrt{L'C}$$

Where $\tau'$ is the build-up time of the intensity of the current in which it moves from 10% to 90% of its nominal value $I_{max}$ U is the pulse voltage L is the inductance seen by the voltage U $I_{max}$ is the intensity of the maximum current reached under the effect of the voltage U C is an equivalent capacity of the electric current pulse generating means And L' is the total equivalent inductance of the entire device (generating means and cell).

So as to obtain a build-up time $\tau$ of the square of the intensity of about or less than 500 ns and in particular between 10 ns and 300 ns, it suffices in practice to use sufficiently known types of high-performance spark switches and generators.

Advantageously and according to the invention, the device is adapted so that the maximum value $I_{max}$ of the electric current established in the electromagnetic cell is less than 1MA and in particular between 2 and 11MA. The voltage U is adapted according to the maximum sought-after intensity $I_{max}$ and according to the inductance of the electromagnetic cell, the build-up time $\tau$ (or $\tau'$) and the dielectric rigidity of the non-conductor.

Furthermore, advantageously and according to the invention, the device comprises means for analysing the mechanical behaviour of the sample, in particular by laser Doppler interferometry. These analysis means can easily be placed opposite the housing in which the sample is fixed.

The invention also extends to a method able to be implemented with a device according to the invention.

The invention thus concerns a method to generate intense and brief magnetic pressure variations, predetermined and controlled and able to be isentropic inside a sample made of a solid material, said method being characterised in that the sample is rigidly secured to a branch of an electromagnetic cell of a device according to the invention and the electric current pulse generating means are switched so as to result in the electromagnetic cell the setting up of an electric current able to generate magnetic pressure forces inside the sample, the build-up time $\tau$ of the square of the intensity of the electric current being between 1 ns and 500 ns and in particular between 10 ns and 300 ns.

In a method according to the invention, the characteristics of the device of the invention are adapted according to the characteristics of the magnetic pressure variations it is desired to create inside the sample.

The invention also concerns a device and method characterised in combination by all or part of the characteristics mentioned above or hereafter.

BRIEF DESCRIPTION OF THE DRAWING

Other aims, characteristics and advantages of the invention shall appear more readily from a reading of the following description with reference to the accompanying drawings on which.

On the figures, the scales, especially concerning thickness, are not observed for the purpose of illustration.

DESCRIPTION OF THE PREFERRED EMBODIMENTS

Figure 1:
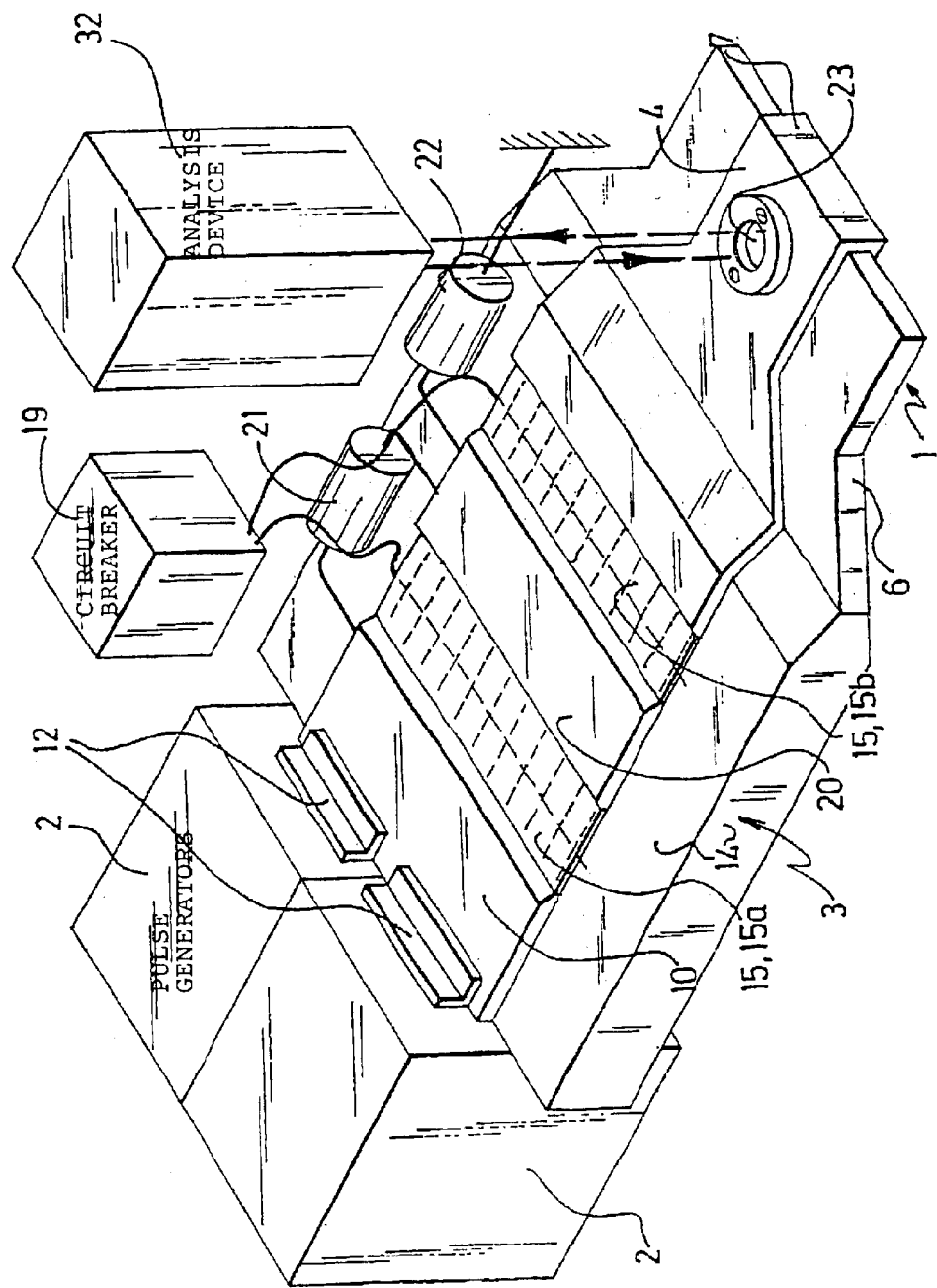
FIG. 1 is a diagrammatic perspective view of a device according to a first embodiment of the invention.
Figure 2:
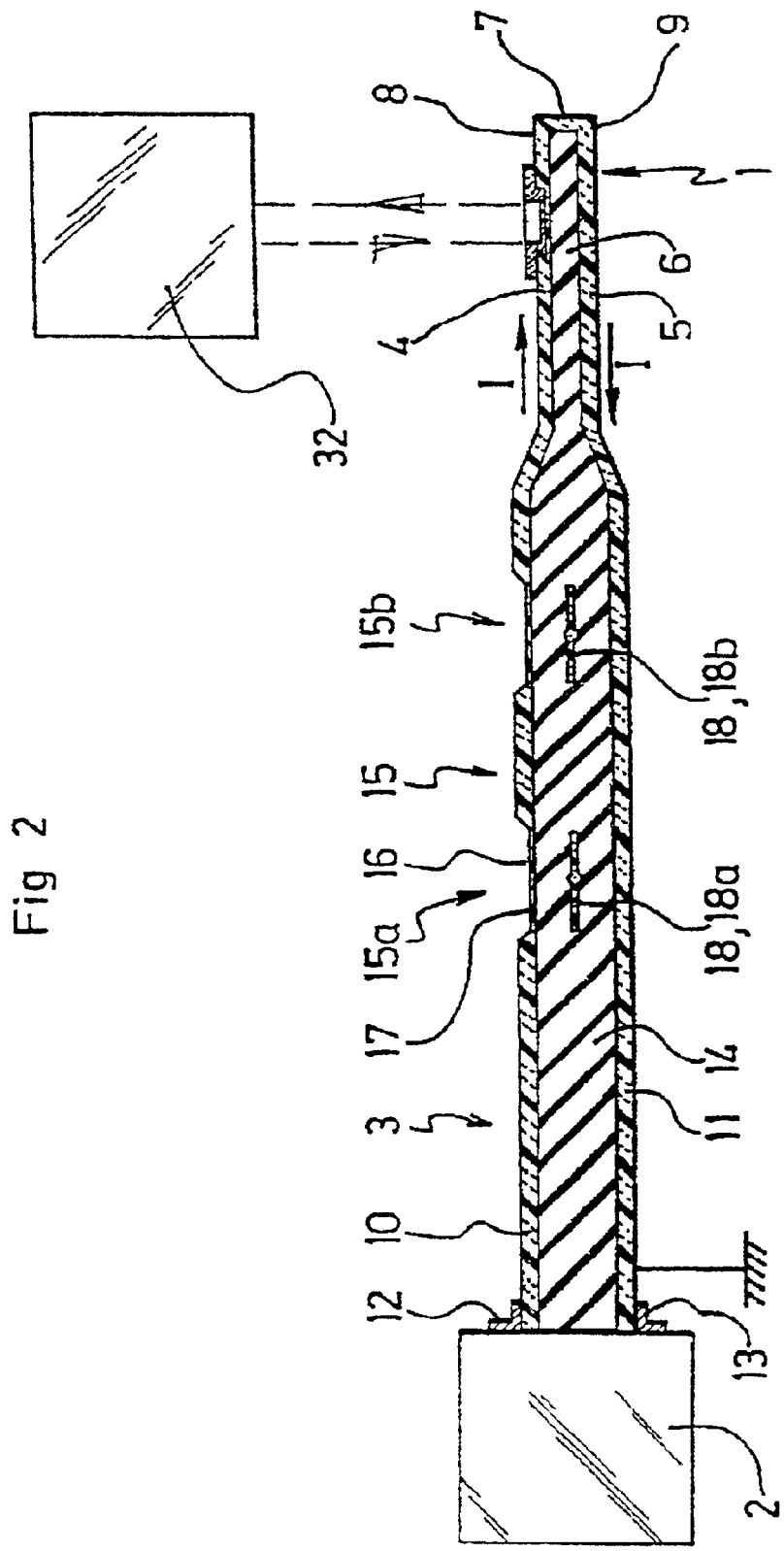
FIG. 2 is a longitudinal cutaway diagrammatic view of the device of the invention shown on FIG. 1.

The device of the invention shown on FIG. 1 includes an electromagnetic cell 1, a set of high power pulsed electric current pulse generators 2, and, between this set of generators 2 and the cell 1, a linking line 3. The electromagnetic cell 1 includes a parallel flat line made of an electrically conductive material including two branches 4, 5 having the shape of rectangular planar plates parallel to each other superimposed opposite each other and separated from each other by a distance less than or equal to 1 mm per insulation layer 6 formed of a solid dielectric material. The two branches 4, 5 are electrically connected to each other by a junction strip 7 extending between the two extreme rectilinear edges 8, 9 of the branches 4, 5. The two branches 4, 5 and the junction strip 7 thus form a parallel flat line having the general shape of an open loop whose longitudinal section has the overall shape of a hairpin (FIG. 2). In the example shown, the junction strip 7 also has the shape of a plate perpendicular to the two branches 4, 5. Nevertheless, it is to be noted that this junction strip 7 could in one variant (not shown) have a curved section, such as a semi-circular one, or have any other shape.

Opposite the junction strip 7, each of the branches 4, 5 is electrically connected to the end of the electrically conductive plates 10, 11 respectively forming the linking line 3, namely a first plate 10 connected to the first electrodes 12 of the generators 2, and a second plate 11 connected to the second electrodes 13 of the generators. An insulation layer 14 made of a solid dielectric material is also inserted between the two plates 10, 11 of the linking line 3. The first plate 10 is provided with a spark switch 15 having a multi-gap multichannel surface able to carry out switching. This surface spark switch is already known (cf. "Low inductance triggered multichannel switch for inductive energy storage generator", B. Etlicher and al, 10th IEEE Pulsed power conference, Alberquerque, N. Mex., 1995, p.243). Each gap of the spark switch 15 includes a cut-off point 16 fitted in the plate 10 along its entire width, an insulation sheet 17 extending between the two edges of the plate 10 opposite separated by said cut-off point 16, and a triggering electrode 18 having the general shape of a comb inserted inside the insulating material 14 under the cut-off point 16. This electrode 18 is connected to a circuit breaker 19 able to polarise the electrode 18 to an adapted high voltage so as to impel disruptive breakdown between the two edges of the cut-off point 16 along the surface of the insulation sheet 17 and the setting up of several parallel electric current lines between the two edges of the cut-off point 16 parallel to the teeth of the comb forming the electrode 18. The circuit breaker 19 is thus basically a pulse voltage source of several tens of kilovolts, but does not deliver any significant electric power.

The number of gaps 15a, 15b of the spark switch 15 placed successively in series depends in particular on the value of the pulse electric voltage which needs to be applied to the electromagnetic cell 1 by the generators 2. In fact, when this value is too high, it is necessary to carry out successively switching from one gap to the other by intermediate plates polarised by intermediate voltages. In the example shown, the spark switch 15 includes two successive gaps 15a, 15b and the intermediate plate 20 separating these two gaps is polarised to an intermediate voltage between the one delivered by the first electrode 12 and that of the second electrode 13 connected to the earth of the generators 2 by a dividing bridge including two resistors 21, 22 having high values (much greater than the entire resistance of the linking line 3 and the electromagnetic cell 1), one resistor 21 connecting the first electrode 12 to the intermediate plate 20 and the other 22 connecting the intermediate plate 20 to the earth. Each gap 15a, 15b includes a comb-shaped triggering electrode 18a, 18b (shown by the dots on FIG. 1) connected to the circuit breaker 19, as described above.

A sample 23 made of a solid material is rigidly fixed to one of the 4 branches of the electromagnetic cell 1. In order to do this, this branch 4 includes a housing fitted recessed so as to receive the sample 23. This housing and thus the sample 23 are placed in at least at an approximately median position on the branch 4, that is at least approximately at the middle of its width. Preferably, advantageously and according to the invention, the housing and the sample 23 are placed at least approximately at the central portion of the branch 4.

Figure 4:
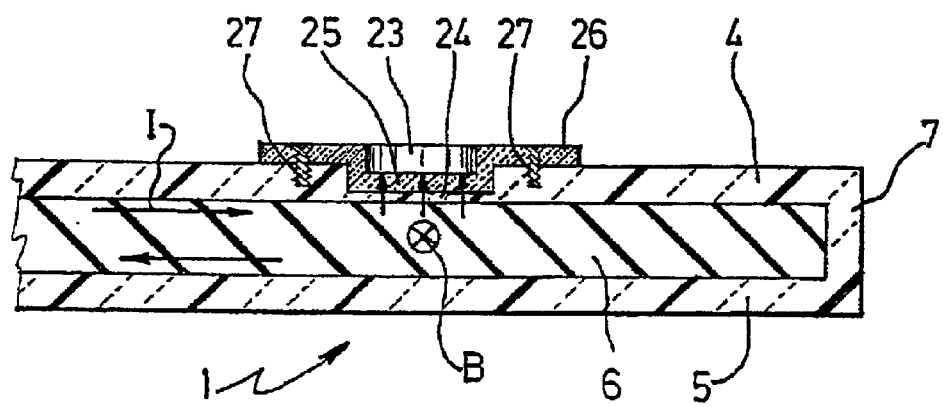
FIG. 4 is a longitudinal cutaway diagrammatic view of an electromagnetic cell according to one variant of a device according to the invention adapted to the case of a non-conductive or poor conductive sample.
Figure 6:
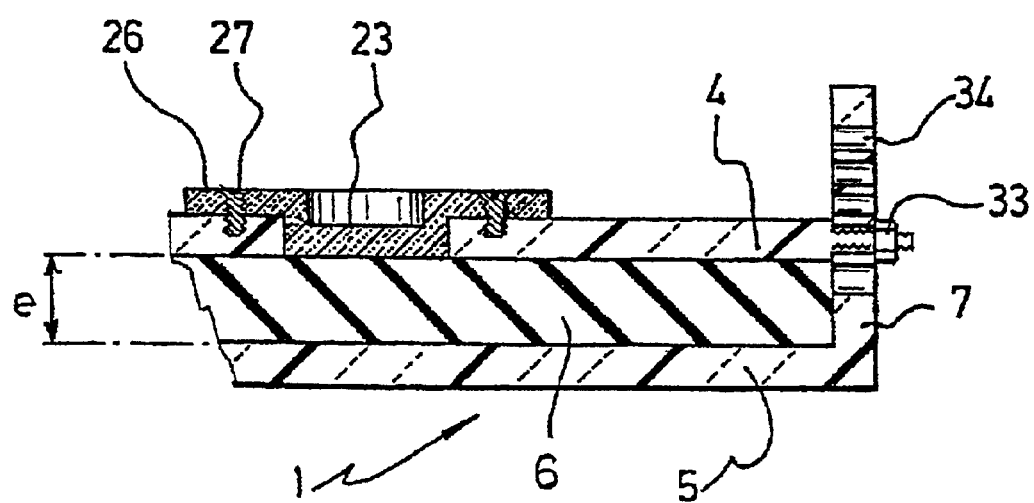
FIG. 6 is a longitudinal cutaway diagrammatic view of an electromagnetic cell according to one variant of a device according to the invention provided with inductance adjustment means.

If the sample 23 is made of a conductive material, the housing receiving said sample can be fitted in the entire thickness of the branch 4, that is as far as the insulation layer 6, the electric current being able to be carried by the sample 23 itself, as shown in the variant of FIG. 6. Otherwise (variant of FIG. 4), the housing is not fully traversing and a conductive wall 24 forms a housing bottom so as to separate the insulation layer 6 from the sample 23 and ensure passage of the electric current opposite the face of the sample 23 in contact with the bottom 24. The thickness of this bottom 24 can be extremely small and for example correspond to skin thickness in which the current circulates in the branch 4.

So as to form the housing receiving the sample 23 and the bottom wall 24, it suffices to make a hollow with suitable dimensions in the thickness of the branch 4.

The sample 23 includes a bottom wall 25 having a relatively fine constant thickness (generally several tenths of millimetres) inside which a magnetic pressure field is to be created when the electric current is to be established through the electromagnetic cell 1 before the sample 23 made of a solid material is destroyed. This bottom wall 25 is prolonged peripherally upwards and laterally below the branch 4 and has the shape of a collar 26 constituting a crown enabling the sample 23 to be fixed to the branch 4 by means of screws 27.

In one variant (not shown), so as to fix the sample 23, it is possible to provide a part separate from the sample 23 itself, forming a fixing crown similar to the one formed by the collar 26.

The electromagnetic cell 1 has a width perpendicular to the direction of circulation of the electric current originating from the generators 2, said width being smaller than the width of the linking line 3 and the cumulated width of the electrodes 12, 13 of the generators 2. Generally speaking, the width of the junction strip 7 is smaller than the cumulated width of the first electrodes 12 or the cumulated width of the second electrodes 13. In this way, the current density increases between the generators 2 and the junction strip 7, that is between the generators 2 and the electromagnetic cell 1 in which the current density is maximum.

As shown on FIG. 1, the electrodes 12, 13 of the generators 2 are simply placed in contact with the conductive plates 10, 11 of the linking line 3.

Figure 3:
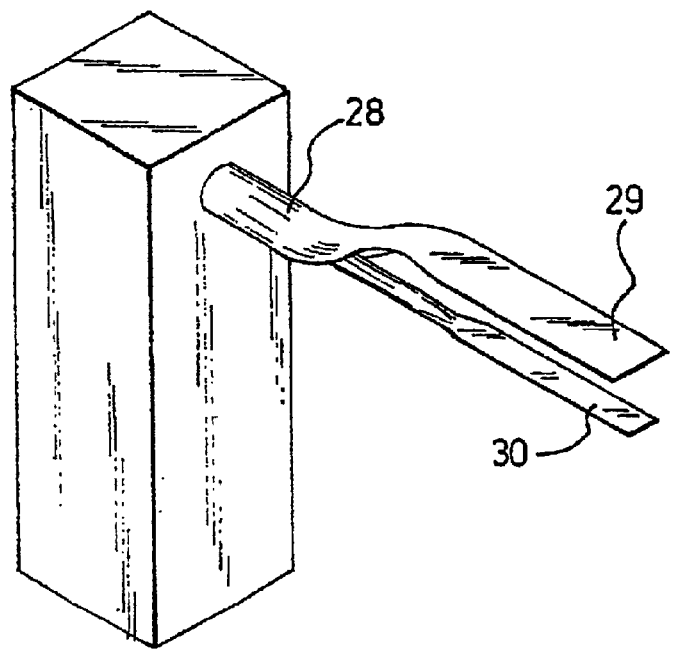
FIG. 3 is a perspective diagrammatic view illustrating the connection of a generator with a coaxial output to an electromagnetic cell of a device according to the invention.

In the case where it is desired to use one or several generators 2 having, not planar electrodes, but a coaxial output, it suffices to transform this coaxial output 28 into two planar electrodes 29, 30, as shown on FIG. 3, thus retaining the value of the area of the cross section of the electrodes.

Figure 5:
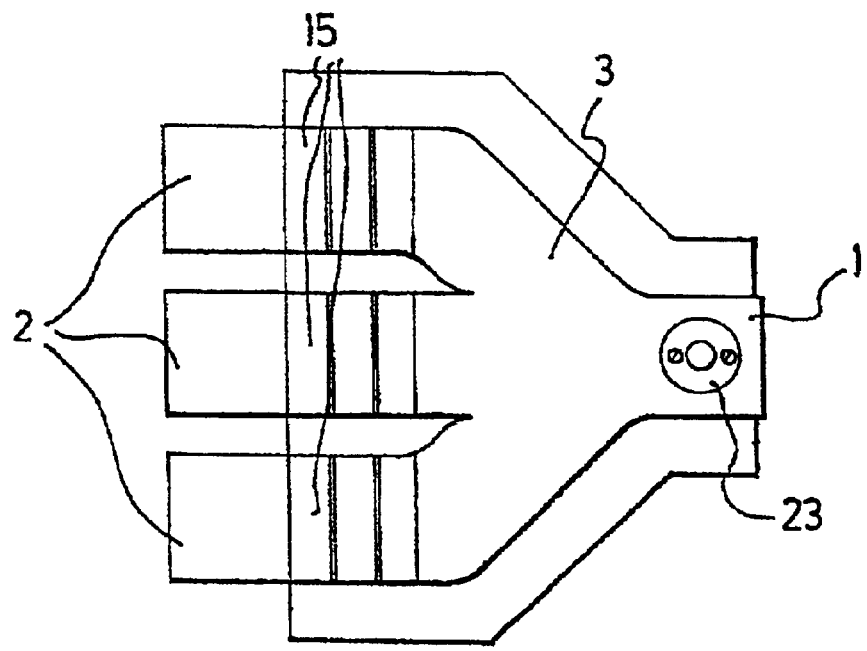
FIG. 5 is a top diagrammatic view of a device according to a second embodiment of the invention.
Figure 7:
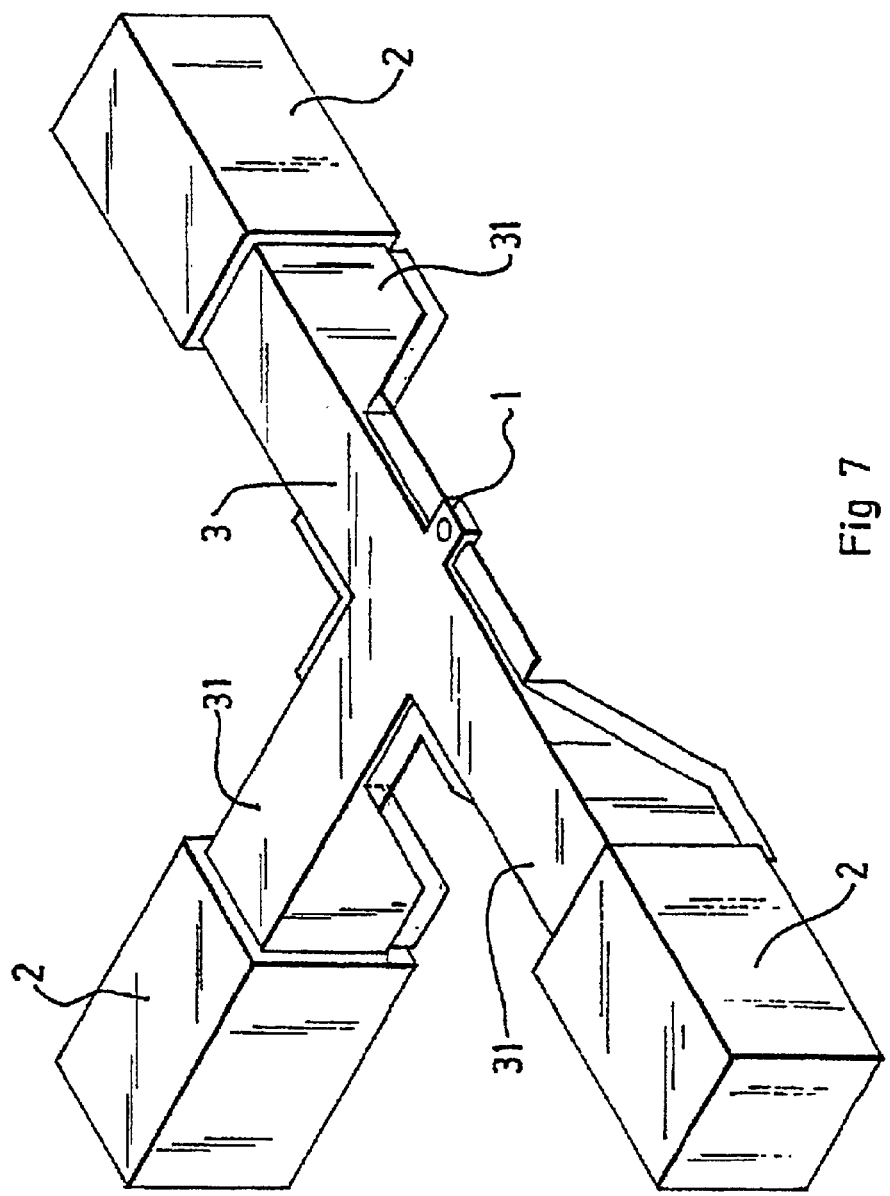
FIG. 7 is a diagrammatic perspective view of a device according to a third embodiment of the invention.

The configuration of the generators 2, the linking line 3 and the switching means 15 with spark switches can be used in a large number of variants. Thus, FIG. 5 diagrammatically shows and seen from above three generators 2 each associated with one spark switch 15 with an individual surface area along three parallel branches of the linking line 3 which meet together inside the plane so as to form the electromagnetic cell bearing the sample 23. FIG. 7 shows another embodiment also including three generators 2 each associated with a volume type spark switch known as a square spark switch 31. Each of the three spark switches 31 is connected to one of the three perpendicular branches forming the linking line 3 with the general shape of a T. The electromagnetic cell 1 is placed as an extension of the junction of the three branches of the linking line 3 in the extension of the main median branch of the T which is perpendicular to the others. The square spark switches 31 are multi-gap multichannel volume spark switches and can for example by embodied as described in the publication "Multi-gap, multi-channel spark switches", Kim A. A. and al, 11$^{th}$ IEEE Pulsed power conference Baltimore, Md., 1997 p. 862. It is possible to use any other embodiment of these multichannel spark switches.

The insulation layer 6 separating the two branches 4, 5 of the electromagnetic cell and the insulation layer 14 separating the plates 10, 11 of the linking line 3 opens laterally onto the side over a sufficient distance so as to avoid any edge disruptive breakdown phenomenon.

As shown on FIG. 2, the thickness of the insulation layer 6 of the electromagnetic cell 1 corresponding to the distance between the two branches 4, 5 of the electromagnetic cell 1 is smaller than that of the insulation layer 14 corresponding to the distance between the two plates 10, 11 of the linking line 3. In fact, the distance separating the two branches 4, 5 of the electromagnetic cell 1 is the smallest distance. In the case where an insulation layer 6 is used formed of a solid or solid/liquid dielectric material placed, in one or several layers, this distance can be less than 1 mm, for example about 500 $\mu$m. Such an extremely small distance has the effect of significantly reducing the inductance of the electromagnetic cell 1 and thus the energy required to establish a high intensity current in a build-up time τ of the square of the intensity lower than 500 ns and especially less than 300 ns inside the electromagnetic cell 1, this high intensity being adapted to create an intense magnetic pressure field inside the sample 23. In this respect, it is to be noted that contrary to what is represented, the thickness of the insulator 6 can be smaller than that of the branches 4, 5.

The simplified equations able to approximately describe the functioning of this electronic cell 1 are the following.

U is the purely inductive voltage applied between the two branches 4, 5, L being the total inductance of the electromagnetic cell 1, $I_{max}$ being the maximum intensity of the electric current established in an electromagnetic cell 1, τ' being the build-up time of the electric intensity of the current from 10% to 90% of its maximum value $I_{max}$, B being the maximum value of the magnetic field, μ being the magnetic permeability of the medium, e being the distance between the branches 4, 5, Em being the dielectric rigidity of the material forming the insulation layer 6 (that is the maximum disruptive breakdown electric field per unit of length thickwise), l being the with of the electromagnetic cell 1 assumed to be equal to its length, C being the equivalent capacity of the generating means, and L' being the total equivalent inductance of the entire device (electric current pulse generating means and electromagnetic cell). In the hypothesis where the length of the electromagnetic cell is equal to its width, the following is obtained:

$$U \approx L.I_{max}/\tau'$$

$$B \approx \mu.I_{max}/l$$

$$L \approx \mu.e$$

$$U \approx Em.e$$

$$I_{max} \approx Em \cdot \frac{\tau}{\mu} \approx U \cdot \tau'/\mu \cdot e$$

$$\tau' \approx \pi/2\sqrt{L'C}$$

Having regard to the Maxwell equations, it is known that the magnetic pressure to be generated inside the sample 23 is proportional to $I^2$ where I is the intensity of the electric current.

Thus, the maximum pressure generated in the sample 23 shall be greater when the dielectric rigidity Em of the insulator is high and when the thickness e between the branches 4, 5 is small. Nevertheless, the maximum voltage able to be applied to the electromagnetic cell 1 is limited by the value of the product of Em by e.

It is to be noted that the dielectric rigidity Em of the material in question is the pulse dielectric rigidity. In practice, there are certain materials formed of a solid/liquid mixture (solid soaked in a liquid) possessing dielectric rigidities of more than 100 kV/mm in a pulse mode for a period of about one microsecond, such as Kapton (registered trademark) commercialised by the company DUPONT DE NEMOURS. This material is a polyimide.

But it is also possible to use a polyester such as Mylar (registered trademark), also commercialised by the company DUPONT DE NEMOURS, or a high density polyethylene.

The branches 4, 5 of the electromagnetic cell 1 typically have a width of about several millimetres, for example between 2 and 15 mm and in particular about 8 mm. The branches of the electromagnetic cell 1 and the linking line 3 can be embodied for example in copper or any other good quality conductor.

By way of example, if e=0.1 mm, Em=200 kV/mm, $I_{max}$=8.10$^6$A, τ'=100 ns, L=0.25 nH, U=20 kV, B is about 1250 Tesla for a sample with a diameter of 5 mm. The maximum magnetic pressure generated inside the material can be about 6.10$^{11}$ Pa. The inductive energy in the electromagnetic cell 1 shall be about 8 kJ.

Moreover, it is established that the magnetic field is extremely homogeneous inside the sample 23. Thus, the same applies to the intensity of the electric current and magnetic pressure field created.

It is to be noted that, in one variant (not shown), the electromagnetic cell 1 can be insulated, not by a insulation layer 6 made of a dielectric material, but by being placed in a vacuum via magnetic insulation. Nevertheless, this technique is cumbersome and complex. In addition, magnetic insulation requires that a certain distance be observed between the branches 4, 5 which in practice is more than 0.5 mm. Accordingly, the inductance of the electromagnetic cell 1 is found to be increased significantly, as well as the maximum polarisation inductive energy of the electromagnetic cell 1 and thus the inductive energy needing to be delivered by the generators 2. In practice, it is nevertheless possible to significantly increase the value of the maximum intensity of the current and thus the maximum magnetic pressure generated inside the sample 23. Normally speaking, it is easily possible to reach values of 11.10$^{11}$ Pa with an inductive energy of between about 40 and 80 kJ.

The generators 2 can be formed of simple capacitors, such as Maxwell capacitors n° 37336 or of any other known pulsed high power generator able to obtain the build-up time τ (or τ') and the voltage value U and the maximum intensity $I_{max}$ (with or without any pulse forming system). Preferably, generators are used having improved yields, small spatial requirement and smaller inductance. From those generators able to be used, it is possible to have: Marx generators, transformers; inductive storage generators; capacitive storage generators; and hybrid inductive and capacitive storage generators.

Furthermore, the sample 23 is analysed by an analysis device 32, for example by Doppler laser interferometry. It is to be noted that the invention can place all appropriate analysis devices opposite the sample 23.

In a device according to the invention, the inductance seen by the generators 2 is extremely weak so that the inductive energy these generators 2 need to produce is also weak. As a result, the generators can be dimensioned with a small spatial requirement and a relative weak output power. Thus, with conventional generators, it is possible to generate inside the sample 23 extremely high magnetic pressure fields over a short but adjustable period. These magnetic pressure fields can be compressions with or without impact and can be isentropic according to the values created. Depending on the voltage delivered by the generators, it is possible to vary the intensity of the current and thus the value of the maximum magnetic pressure without varying the period of application of the pressure field. If the distance e between the branches 4, 5 is varied, for example with the device variant shown on FIG. 6, it is then possible to adjust the value of the inductance L and thus that of the maximum current $I_{max}$ and the build-up time τ' (or τ). As can be seen on FIG. 6, the branch 4 is associated with the junction strip 7 by bolts 33 which prolong this branch 4 and traverse the bores 34 fitted through the junction strip 7 which itself is extended upwards. Several bore lines 34 are provided in the junction strip 7 according to the distance it is desired to give between the branches 4, 5. As a variant, it is also possible to create an additional inductance in the linking line 3 or in the electromagnetic cell 1 by inserting means forming a variable inductance, such as a height-adjustable bridge.

A large number of variants are possible with respect to the embodiments described and shown given solely by way of non-restrictive examples.

What is claimed is:

1. A device for generating intense and brief magnetic pressure variations, predetermined and controlled, able to be isentropic inside a sample (23) made of a solid material, comprising:

means (2, 3) for generating current pulses of the pulsed high power type; and an electromagnetic cell (1) connected to the electric current pulse generating means (2, 3), said electromagnetic cell (1) bearing the sample (23) and being adapted so as to have the sample (23) subjected to electromagnetic energy pulses resulting from the application to the electromagnetic cell (1) of electric current pulses originating from the electric current pulse generating means (2, 3), wherein the electromagnetic cell (1) includes a parallel flat line made of a conductive material including two branches (4, 5) with the shape of planar plates having the same shapes and dimensions and separated from each other by a distance less than or equal to 3 mm, one of said branches (4) bearing the sample (23) fixed rigidly to this branch (4), these two branches (4, 5) being electrically connected to each other by an end junction strip (7) and electrically connected opposite the end junction strip (7) to the electric current pulse generating means (2, 3) so as to allow an electric current to be established circulating from the electric current pulse generating means (2, 3) in one branch (4) and then into the end strip (7) and then into the other branch (5) so as to come back to the electric current pulse generating means (2, 3), and wherein the electric current pulse generating means (2, 3) and the electromagnetic cell (1) are adapted so that the build-up time τ in which the square of the intensity of the electric current circulating in the electromagnetic cell (1) moves from 10% to 90% of its maximum value $I_{max}^2$ namely between 1 ns and 500 ns.

2. Device according to claim 1, characterised in that the electromagnetic cell (1) is adapted to have an inductance of less than 4 nH.

3. Device according to claim 1, characterised in that the two branches (4, 5) are isolated from each other by a dielectric material (6).

4. Device according to claim 3, characterised in that the dielectric material (6) is solid or solid/liquid.

5. Device according to claim 3, characterised in that the dielectric material (6) has a pulse dielectric rigidity of more than 100 kV/mm.

6. Device according to claim 3, characterised in that the dielectric material (6) extends laterally beyond the branches (4, 5) so as to prevent any edge disruptive breakdowns.

7. Device according to claim 3, characterised in that the dielectric material (6) is selected from a polyimide, a polyester or a high density polyethylene.

8. Device according to claim 3, characterised in that the distance between the two branches (4, 5) is less than 1 mm.

9. Device according to claim 3, characterised in that the electromagnetic cell (1) is adapted to have an inductance of less than 2 nH.

10. Device according to claim 1, characterised in that the electric current pulse generating means (2, 3) comprise:

at least one pulsed high power electric current generator (2) including two outgoing electrodes (12, 13) known as first (12) and second (13) outgoing electrodes, an electric linking line (3) including a first conductive plate (10) extending between the first outgoing electrode (12) of reach generator (2) and one (4) of the branches of the electromagnetic cell (1), and a second conductive plate (11) extending between the second outgoing electrode (13) and the other branch (5) of the electromagnetic cell (1).

11. Device according to claim 10, characterised in that the cross section of the junction strip (7) perpendicular to the direction of the electric current is smaller than the cumulated cross section of the first (12) or second (13) electrodes so that the electric current density reaches its maximum value in the junction strip (7).

12. Device according to claim 11, characterised in that the width of the junction strip (7) is smaller than the cumulated width of the first (12) or second (13) electrodes.

13. Device according to claim 11, wherein the two branches (4, 5) are rectangular, the junction strip (7) connects two rectilinear edges (8, 9) of the two branches (4, 5), and the plates (10, 11) of the electric linking line (3) have a convergent shape concerning its width and/or thickness so that the current density has its maximum value in the branches (4, 5) of the electromagnetic cell (1).

14. Device according to claim 10, characterised in that the plates (10, 11) of the linking line (3) have overall the same shapes and dimensions, are parallel to each other and are superimposed opposite each other, separated and isolated from each other.

15. Device according to claim 10, characterised in that the plates (10, 11) of the linking line (3) extend into the prolongation of the branches (4, 5) of the electromagnetic cell (1).

16. Device according to claim 10, characterised in that the linking line (3) is adapted so as to have an inductance of less than 5 nH.

17. Device according to claim 10, characterised in that a multichannel spark switch (15, 31) is inserted between each generator (2) and the electromagnetic cell (1).

18. Device according to claim 17, characterised in that for each generator (2) an individual multichannel spark switch (15, 31) is inserted between the first outgoing electrode (12) of this generator (2) and the first plate (10) of the linking line (3).

19. Device according to claim 1, characterised in that the electric current pulse generating means (2, 3) include at least one multichannel spark switch (15, 31) able to distribute the electric energy along the cross section of the branches (4, 5) of the electromagnetic cell (1).

20. Device according to claim 19, characterised in that it includes at least one set of several generators (2) and in that a common multichannel spark switch (15) is inserted between all the first electrodes (12) of the generators (2) of the same set and the first plate (10) of the linking line (3).

21. Device according to claim 19, characterised in that it includes at least one series multi-gap spark switch (15, 31).

22. Device according to claim 19, characterised in that it includes several spark switches (15, 31) in parallel.

23. Device according to claim 1, characterised in that the sample (23) is placed and rigidly fixed in a housing of the branch (4) bearing it.

24. Device according to claim 23, characterised in that the housing opens on the side of the space separating the two branches (4, 5) from each other so that a sample (23) made of a conductive material can be placed in the housing so as to be in electric liaison with the branch (4) bearing it, this sample (23) having one face in contact with the space separating the two branches (4, 5) from each other, especially in contact with the dielectric material (6).

25. Device according to claim 23, characterised in that the housing has a bottom (24) forming a conductive wall able to separate a sample (23) or material made of a conductive material or one made of a poor conductive material placed in the housing from the space separating the two branches (4, 5) from each other, especially from the dielectric material (6).

26. Device according to claim 25, characterised in that the conductive wall (2, 4) has a thickness smaller than that of the branch (4) bearing it.

27. Device according to claim 1, characterised in that it includes means (33, 34) for adjusting the value of the inductance of the electromagnetic cell (1) and/or of the electric current pulse generating means (2, 3).

28. Device according to claim 1, characterised in that it includes means (33, 34) for adjusting the distance (e) between the two branches (4, 5).

29. Device according to claim 1, characterised in that it comprises means (32) for analysing the mechanical behaviour of the sample (23), especially via laser Doppler interferometry.

30. Method to generate intense and brief magnetic pressure variations, predetermined and controlled, able to be isentropic inside a sample (23) made of a solid material, characterised in that the sample (23) is rigidly secured to a branch (4) of an electromagnetic cell (1) of a device according to claim 1, and electric current pulse generating means (2, 3) are switched so as to result in the electromagnetic cell (1) the setting up of an electric current able to generate magnetic pressure forces inside the sample (23), the build-up time $\tau$ of the square of the intensity of the electric current being between 1 ns and 500 ns.

* * * * *